United States Patent
Conradsen et al.

(10) Patent No.: US 9,949,654 B2
(45) Date of Patent: Apr. 24, 2018

(54) METHOD FOR DETECTING SEIZURES

(75) Inventors: Isa Conradsen, Copenhagen (DK); Kim Gomme Gommesen, Odense (DK); Karsten Hoppe, Copenhagen (DK)

(73) Assignee: BRAIN SENTINEL, INC., San Antonio, TX (US)

( * ) Notice: Subject to any disclaimer, the term of this patent is extended or adjusted under 35 U.S.C. 154(b) by 405 days.

(21) Appl. No.: 14/233,904

(22) PCT Filed: Jun. 27, 2012

(86) PCT No.: PCT/DK2012/050215
§ 371 (c)(1),
(2), (4) Date: Jan. 31, 2014

(87) PCT Pub. No.: WO2013/010543
PCT Pub. Date: Jan. 24, 2013

(65) Prior Publication Data
US 2014/0163413 A1   Jun. 12, 2014

(30) Foreign Application Priority Data
Jul. 19, 2011 (DK) .................. 2011 00556

(51) Int. Cl.
*A61B 5/04* (2006.01)
*A61B 5/0488* (2006.01)
(Continued)

(52) U.S. Cl.
CPC ...... *A61B 5/04014* (2013.01); *A61B 5/04004* (2013.01); *A61B 5/04012* (2013.01);
(Continued)

(58) Field of Classification Search
CPC .......................... A61B 5/04014; A61B 5/4094
See application file for complete search history.

(56) References Cited

U.S. PATENT DOCUMENTS 5,542,430 A * 8/1996 Farrugia ............. A61B 5/0464
                                                         128/924
6,950,702 B2   9/2005 Sweeney
(Continued)

FOREIGN PATENT DOCUMENTS

| WO | 2004/006763 A2 | 1/2004 |
| WO | 2005/018448 A1 | 3/2005 |

(Continued)

OTHER PUBLICATIONS

Potvin, J.R., and S.H.M. Brown. "Less is more: high pass filtering, to remove up to 99% of the surface EMG signal power, improves EMG-based biceps brachii muscle force estimate." Journal of Electromyography and Kinesiology 14.3 (2004): 389-399.*

(Continued)

*Primary Examiner* — Michael C Stout
*Assistant Examiner* — Nicholas E Kolderman
(74) *Attorney, Agent, or Firm* — James C. Wray

(57) ABSTRACT

A method and system for detecting the onset of seizures comprising a measuring unit having one or more sensors for detecting the electromyographic signal of one or more muscles of the user. The sensors are connected to a pre-processing module comprising a high-pass filter which filters out noise and motion artefacts related to normal muscle activities. The pre-processing module is connected to a feature extraction module comprising a threshold detector which counts the number of crossings with a hysteresis within a predetermined time window. The feature extraction module is connected to a classification module which compares the extracted features to a first and second threshold and generates an event signal if the extracted features are above the first and second threshold.

24 Claims, 1 Drawing Sheet

Figure 1:
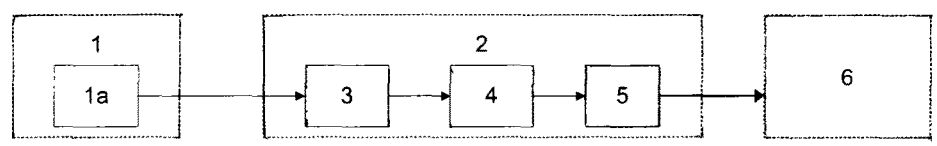

(51) Int. Cl.
*A61B 5/11* (2006.01)
*A61B 5/00* (2006.01)

(52) U.S. Cl.
CPC ........ *A61B 5/04015* (2013.01); *A61B 5/0488* (2013.01); *A61B 5/1123* (2013.01); *A61B 5/4094* (2013.01)

(56) References Cited

U.S. PATENT DOCUMENTS

| | | |
|---|---|---|
| 2004/0010200 A1 | 1/2004 | Sweeney |
| 2004/0230105 A1 | 11/2004 | Geva et al. |
| 2007/0150025 A1 | 6/2007 | DiLorenzo et al. |
| 2007/0162086 A1 | 7/2007 | DiLorenzo et al. |
| 2008/0269835 A1 | 10/2008 | Carlson et al. |
| 2009/0062696 A1* | 3/2009 | Nathan ............ A61B 5/1107 600/595 |
| 2010/0030088 A1 | 2/2010 | Carney et al. |
| 2010/0137735 A1* | 6/2010 | Hoppe ............ A61B 5/0002 600/546 |

FOREIGN PATENT DOCUMENTS

| | | |
|---|---|---|
| WO | 2007/034476 A2 | 3/2007 |
| WO | 2007/079181 A2 | 7/2007 |
| WO | 2007/143234 A2 | 12/2007 |
| WO | 2008/131782 A1 | 11/2008 |

OTHER PUBLICATIONS

Shiau, Deng-Shan, et al. "Signal regularity-based automated seizure detection system for scalp EEG monitoring." Cybernetics and systems analysis 46.6 (2010): 922-935.*
Motion Lab Systems Software: EMG Analysis. Motion Lab Systems, Inc., May 11, 2008. Web. Apr. 22, 2016. <https%3A%2F%2Fweb.archive.org%2Fweb%2F20080511202020%2Fhttp%3A%2F%2Fwww.motion-labs.com%2Fsoftware_emg_analysis.html>.*

* cited by examiner

METHOD FOR DETECTING SEIZURES

TECHNICAL FIELD

This application claims the benefit of Danish Application No. PA 2011 00556 filed Jul. 19, 2011, and PCT/DK2012/050215 filed Jun. 27, 2012, International Publication No. WO 2013/010543, which are hereby incorporated by reference in their entirety as if fully set forth herein.

The invention also relates to a method for indicating the onset of seizures, such as epileptic seizures, comprising the steps of detecting one or more electromyographic signals generated by at least one muscle on the body of a user by means of a measuring unit, processing and analysing the detected signal by means of a data processing unit in which the detected signal is filtered by means of a high-pass filter and a first number of predetermined time windows is applied to the filtered signal, and generating an event signal by means of the data processing unit and triggering an event based on the event signal.

The invention also relates to a method for indicating the onset of seizures, such as epileptic seizures, comprising the steps of detecting one or more electromyographic signals generated by at least one muscle on the body of a user by means of a measuring unit, processing and analysing the detected signal by means of a data processing unit in which the detected signal is filtered by means of a high-pass filter and a first number of predetermined time windows is applied to the filtered signal, and generating an event signal by means of the data processing unit (2) and triggering an event based on the event signal.

PRIOR ART

Today there is a need for a way to improve the detection of seizure onsets in order to improve treatment or to alert caretakers or the patient of a seizure in order to prevent potential dangerous situations associated with a seizure. Seizures, such as epileptic seizures, can occur as partial or generalized seizures or a combination of both, where generalized seizures among other can occur as tonic, clonic, or tonic-clonic seizures. In a tonic-clonic seizure it starts with a tonic phase which then develops into a clonic phase.

Different methods or algorithms for detecting seizure onsets are described in the literature. An example of such is disclosed in WO 2008/131782 A1 which detects epileptic seizures by evaluating a sensed EMG signal over a number of time windows, if the sensed EMG signal is over a threshold value within the first time window, where the threshold value is determined according to the maximum voluntary contraction of the user. The algorithm has the disadvantage that the parameters have to be adjusted to each individual person in order to reduce the number of false positives and accurately detect the seizure.

US 2007/0142873 A1 describes an adaptive method and system for detecting seizures by sensing iEEG signals which is used in a feedback loop to administer a drop or give a simulate to counteract the seizure. The parameters used to detect the seizures are determined by using a time consuming and very complex data process, where the system performs several measurements with different parameter settings from which the best parameter settings are selected. This system requires the desired signals to be captured by multiple channels in order to accurately detect the signals and to reduce the number of false positives. Furthermore, this method uses an invasive procedure to place the iEEG sensors on the body.

WO 2007/079181 A2 describes an epileptic seizure detection method and system comprising a sensor unit having multiple intracranial EEG electrodes connected to a processor unit in which a prediction algorithm is implemented. The prediction algorithm determines the probability of having a seizure within the near future by combining multiple features extracted from the sensed EEG signals. The processor unit may comprise any number of components used to process the signals, but it does not disclose an exemplary embodiment of the prediction algorithm. Furthermore, this method requires the signal to be measured at multiple locations in order to predict seizures and uses a training module/process to adjust the parameters used to predict seizures.

US 2004/0230105 A1 describes a method and system for predicting epileptic seizures which may use an EMG sensor to detect a biomedical signal connected to a processor which processes the signals using a segmentation algorithm. Various features are then extracted and analysed in a prediction algorithm using a set of HMM models to predict a seizure. The method uses an automatic training algorithm to adjust the parameters of each HMM model. This system uses a complex and time-consuming method to detect seizures which are not suited for implementation in a small battery powered device attached to the body of a user. Furthermore, this method requires the detection of multiple signals at multiple locations and the adjustment of the parameters for each individual user.

WO 2007/143234 A2 discloses an implantable system for detecting epileptic seizures comprising a sensor unit having multiple intracranial EEG electrodes connected to a processing unit. The processing unit applies a number of time windows and amplitude ranges to the EEG-signals and generates an output signal of +1, 0 or −1. The processing unit then determines a rolling sum of the output signals over a certain number of time windows. The thresholds defining the amplitude ranges need to be adjusted to the individual user in order to reduce false detections. The system requires multiple EEG electrodes to be implanted in the scull and requires a lot of data processing in order to detect the onset of seizures. This increases the health risk for the patient and reduces the operation time of the device.

Object Of The Invention

The invention solves these problems of the closest prior art by providing a method indicating the onset of seizures characterized by counting the number of crossings between the filtered signal and a predetermined hysteresis value defining a positive and a negative threshold value within each of the predetermined time windows, and generating a second number of time windows having a count above the first threshold value, further comparing the second number of time windows to a second threshold value, and generating the event signal if the second number of time windows is above the second threshold value. The number of crossings, e.g. zero-crossings, is counted in the positive and negative direction when the filtered signal alternately passes the positive and negative values of the hysteresis value.

This method can be implemented as a generic algorithm in a seizure detection or monitoring device without having to calibrate the parameters for each individual user first. The seizure detection method has a low false detection rate and a short latency, so that seizures can be detected faster and more accurately. Furthermore, this enables seizures to be detected by using only one measuring channel, thus reducing the complexity of the detection system and the number of components needed to detect seizures.

According to one embodiment, overlapping time windows of a predetermined length are applied to the filtered signal where a first time window overlaps a second time window with a predetermined overlap. This enables the length and shape of the time windows to be selected so that the detection system has a sufficiently short latency. This also enables the overlap of the time windows to be selected so that the data analysis is improved.

This enables the first and second threshold values to be selected so that all seizures are detected while reducing the number of false positives to a minimum and ensuring a short latency for the detection system. This also enables the first and second threshold values to be determined according to the seizure characteristics detected at that measuring position in order to more accurately detect the seizures.

According to one embodiment, at least a second measuring unit detects the muscle activities of one or more muscles on the body of the user or another signal characteristic of a seizure, and at least a second data processing unit processes and analyses the detected signal of the second measuring unit and generates an output signal indicating whether the detected signal is above a third threshold value or not. According to a specific embodiment, the output signals of the classification modules in the data processing units are transmitted to an evaluation module which generates the event signal if two or more of the output signals have a high output value or if a weighted sum of the output signals is above a fourth threshold value. This improves the detection of seizures by comparing the detected signal to other signals which are detected at different locations, thus reducing the number of false positives.

According to one embodiment, the event signal is transmitted to an alarm unit which generates an alarm or an alarm message based on the event signal. This enables the algorithm to inform or alert the user or an external caretaker that a seizure is occurring so that the necessary actions can be taken.

The invention also solves these problems by providing a system for detecting the onset of seizures characterized in that the feature extraction module is configured to count a number of crossings between the filtered signal and a predetermined hysteresis value defining a positive and a negative threshold value within each of the predetermined time windows, and the classification module is configured to compare the count of crossings to a first threshold value, generate a second number of time windows having a count above the first threshold value, further compare the second number of time windows with a second threshold value and hereby generate the event signal if the second number of time windows is above the second threshold value.

This enables the detection system to be implemented as a generic detection system which does not require the parameters for the algorithm to be calibrated for each individual user. This also enables the system to detect seizures by using only one measuring channel, thus reducing the complexity of the detection system and the number of components needed to detect seizures. This seizure detection system has a low false detection rate and a short latency so that seizures can be detected faster and more accurately.

According to a specific embodiment, the cut-off frequency is above 100Hz, preferably between 100Hz and 200Hz. This enables the system to filter out most of the noise and motion artefacts, which do not relate to the seizure, before analysing the detected signal.

According to a specific embodiment, the hysteresis value is between ±0µV and ±500µV, preferably ±20µV and ±250µV. This enables the hysteresis value to be selected so that low-level noise and motion artefacts, which are not removed by the pre-processing module, have no or a minimum effect on the counts. The threshold detector mainly detects the frequency of the filtered signal if the hysteresis has a low value, whereas the threshold detector detects both the frequency and the amplitude of the filtered signal if the hysteresis has a high value.

According to a specific embodiment, the predetermined time windows are configured as overlapping time windows having a predetermined overlap and length. A first time window overlaps a second time window, and the overlap is between 0 and 95%, preferably between 50 and 75%. According to another specific embodiment, the time windows have a length between 0.25 and 2 sec. This enables the length of the time windows to be selected so that the detection system has a sufficiently short latency. This also enables the overlap of the time windows to be selected according to the shape of the time window so that the data analysis is improved.

According to a specific embodiment, the first threshold is between 100 and 400, preferably between 240 and 300, and the second threshold is between 1 and 40, preferably between 10 and 25. This enables the first and second threshold values to be selected so that all seizures are detected while reducing the number of false positives to a minimum and ensuring a short latency for the detection system. This also enables the first and second threshold values to be determined according to the seizure characteristics detected at that measuring position in order to more accurately detect the seizures.

According to one embodiment, the system comprises at least a second measuring unit which is configured to detect the muscle activities of one or more muscles on the body of the user or another signal characteristic of a seizure, and at least a second data processing unit which is connected to the second measuring unit and configured to process and analyse the detected signal of the second measuring unit and further configured to generate an output signal indicating whether the detected signal is above a third threshold value or not. According to a specific embodiment, the classification modules in the data processing units are further connected to an evaluation module which is configured to generate the event signal, if two or more of the output signals from the classification modules have a high output value or if a weighted sum of the output signals is above a fourth threshold value. This improves the detection of seizures by comparing the detected signal to other signals which are detected at different locations, thus reducing the number of false positives.

According to one embodiment, the system further comprises an alarm unit connected to the data processing unit, wherein the alarm unit is configured to generate an alarm or an alarm message based on the event signal. This enables the detection system to inform and alert the user or an external caretaker that a seizure is occurring, thereby allowing the person to take proper action. This also enables the alarm unit to be integrated into the unit which can be easily attached to or placed on the body of the user.

The invention also describes the use of the method or system to detect seizures having tonic activity, such as tonic-clonic seizures.

THE DRAWINGS

Figure 2:
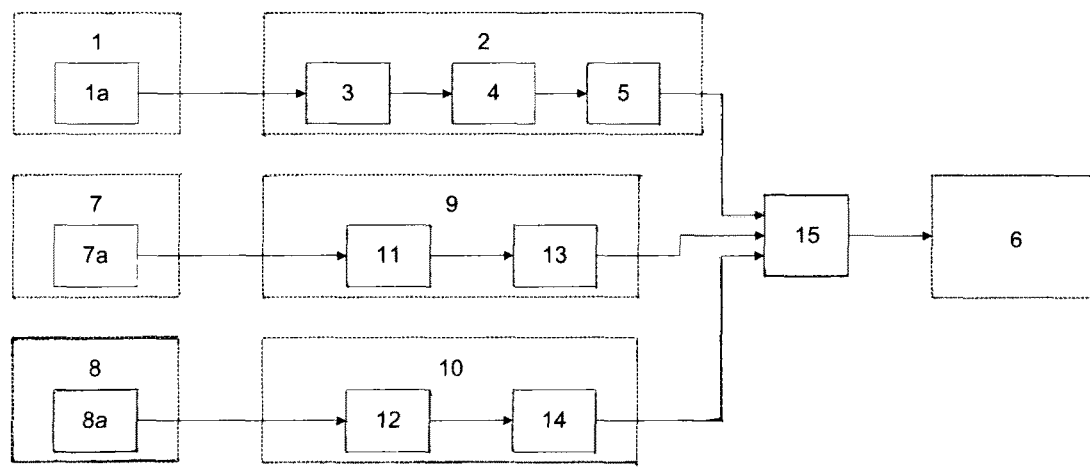

The embodiments of the invention will now be described with reference to the drawings, in which FIG. 1 shows a first embodiment of the seizure detection system according to the invention, and FIG. 2 shows a second embodiment of the seizure detection system according to the invention.

DESCRIPTION OF EXEMPLARY EMBODIMENT

FIG. 1 shows a first embodiment of the detection system which comprises a measuring unit 1 having one or more sensors 1a for sensing the muscle activities generated by one or more muscles, i.e. the skeletal muscles, on the body of a user. The sensors 1a may be configured as electromyographic sensors. The sensors 1a may be integrated into the measuring unit 1, which may be attached or fixed to the body by using an adhesive agent or a fixating band or strap, or alternatively may be placed at different measuring positions and connected to the measuring unit 1 by a wired or wireless connection. The sensors 1a may be connected to a controller and a memory module, and data from the sensors may be stored in the memory module before being transmitted to a data processing unit 2 either periodically, continuously or on request from the data processing unit 2. In a preferred embodiment the measuring unit 1 uses a single measuring channel to detect the electromyographic signal. This enables the sensors to be easily placed at the measuring positions without using any invasive procedures.

The detected data are then transmitted via a wired or wireless connection to the data processing unit 2 which processes and analyses the data. The data processing unit 2 may be an external device or integrated into the measuring unit 1. The detected data are transmitted to a pre-processing module 3 comprising filter means for filtering out noise and motion artefacts which relate to normal muscle activities. The filter means may be configured as a high-pass filter with a predetermined cut-off frequency which filters out most of the noise and motion artefacts not related to the seizure. Studies have shown that all or most of the data relating to the seizure are situated in a frequency band above 100Hz, while all or most of the noise and motion artefacts and discriminating it from normal activity are situated in a frequency band of 0Hz and 20Hz. The cut-off frequency may be selected as any frequency between the upper frequency of the lower frequency band and the lower frequency of the upper frequency band, i.e. between 20Hz and 200Hz, preferably between 100Hz and 200Hz. The cut-off frequency may be selected according to the desired order of the high-pass filter. The pre-processing module 3 may comprise a biasing circuitry which removes any bias so that the filtered signal is symmetric around zero. In a preferred embodiment the cut-off frequency for the filter means is selected to be 150Hz or 170Hz.

The filtered data are then transmitted to a feature extraction module 4 which extracts one or more predetermined features. The feature extraction module 4 applies a number of predetermined time windows to the filtered data. The time windows may be configured as overlapping time windows with a predetermined overlap and length. The time windows may be shaped as a rectangular, a triangular, a cosine, a sinc or another type of window where the overlaps have a rectangular, a triangular or another shape. In order to improve the data analysis, the time windows may have an overlap between 0% and 95%, preferably between 50% and 75%. The length of the time windows is selected so that the detection system has a sufficiently short latency, i.e. the length may be between 0.25 sec and 2 sec. In a preferred embodiment the time window is selected to have an overlap of 75% and a length of 1 sec.

The feature extraction module 4 uses a threshold detector to count the number of crossings, i.e. the zero-crossings, between the amplitude of the filtered signal and at least one predetermined threshold value within each time window. The threshold detector may be configured as a threshold detector with a predetermined hysteresis value, i.e. a positive and a negative threshold value. The hysteresis value may be selected so that low-level noise and motion artefacts, which are not removed by the pre-processing module 3, have no or a minimum effect on the counts. The hysteresis value may be selected within a range of ±0µV and ±500µV, preferably within ±20µV and ±250µV. In a preferred embodiment the threshold detector has a hysteresis value of ±50µV or ±100µV. If the hysteresis has a low value, the threshold detector mainly detects the frequency of the filtered signal, while the threshold detector detects both the frequency and the amplitude of the filtered signal if the hysteresis has a high value.

The feature extraction module 4 transmits the count for each time window to a classification module 5 which evaluates the extracted features and generates an event signal if at least one of the extracted features is above a threshold value. The classification module 5 compares the count for each time window to a first threshold value and generates an event signal if the count is above the threshold value. Alternatively, the classification module 5 may compare the number of time windows, which has a count above the first threshold value, to a second threshold value and generate an event signal if the number of time windows is above the second threshold value. The number of time windows with a count above the first threshold value may be determined by counting the number of consecutive and/or non-consecutive time windows within a second predetermined time window.

The first and second threshold may be adjusted in order to more accurately detect the seizures. The thresholds may be determined according to the seizure characteristics detected at that measuring position.

Studies have shown that a tonic-clonic seizure generates a high number of crossings (counts) in the tonic phase, which then drops to a lower number at the beginning of the clonic phase. The first threshold value for the number of crossings may be between 100 and 400, preferably between 240 and 300. The second threshold value for the number of time windows may be between 1 and 40, preferably between 10 and 25. The first and second threshold values may be selected so that all seizures are detected while reducing the number of false positives to a minimum and ensuring a short latency for the detection system. In a preferred embodiment the first threshold value is selected to be 260 and the second threshold value is selected to be 15.

The event signal triggers an event which informs or alerts the user or an external caretaker that a seizure is occurring. The event signal may be transmitted to an alarm unit 6 by a wired or wireless connection. The alarm unit 6 may be an external device or integrated into the measuring unit 1 or the data processing unit 2. The alarm unit 6 may generate one or more types of alarms or messages, i.e. an audio, a visual, a vibrating alarm, an alarm message, or any combination thereof. The measuring units 1, the data processing units 2, and optionally the alarm unit 6 may be integrated into a single unit which can be easily attached to or placed on the body.

FIG. 2 shows a second embodiment of the detection system, where the reference numbers are the same as in FIG. 1. The detection system comprises a number of measuring units 1, 7, 8, which are placed at different measuring positions on the body. The measuring units 7, 8 may have the same configuration as the measuring unit 1 or different configurations. The measuring unit 1, 7, 8 comprises one or more sensors 1a, 7a, 8a for measuring the muscle activities generated by one or more muscles, i.e. skeletal muscles. Alternatively, the measuring units 1, 7, 8 may comprise different types of sensors, i.e. EMG, MMG or PMG, for measuring the muscle activity or may comprise at least one other sensor for measuring another type of signal related to a seizure, i.e. respiration, heart rate or galvanic skin response. The sensors may be easily placed at the measuring positions without using any invasive procedures by using an adhesive agent or a fixating band or strap. This enables the system to improve the detection of seizures and reduce the number of false positives by comparing the detected signal with other signals which are detected at different locations.

The detection system may comprise a number of data processing unit 2, 9, 10, which are connected to each of the measuring units 1, 7, 8. The data processing unit 9, 10 may have the same configuration as the data processing unit 2 or a different configuration. The data processing unit 2, 9, 10 may comprise processing means 3, 4, 11, 12 which analyses and extracts one or more features or patterns from the measured signals, and a classification module 5, 13, 14, which compares the extracted features or patterns to one or more threshold values and generates an output signal, i.e. a high or a low output signal, indicating whether a seizure is present or not. The outputs of each classification modules 5, 13, 14 in the data processing units 2, 9, 10 are transmitted by a wired or wireless connection to an evaluation module 15 which evaluates the output signals and generates an event signal if a seizure is detected. The evaluation module 15 may generate an event signal if two or more of the output signals are high. Alternatively, the evaluation module 15 may apply a predetermined weighing factor to each of the output signals and generate an event signal if the sum of these weighted outputs is above a third threshold value. The event signal is then transmitted by a wired or wireless connection to the alarm unit 6 which informs or alerts the user or an external caretaker that a seizure is occurring.

The data processing units 2, 9, 10 may be arranged as parallel pipelines in a common data processing unit or as separate data processing units which are connected to the evaluation module. The evaluation module 15 may be integrated into the common data processing unit or into one of the separate data processing units.

The described method in FIGS. 1 and 2 for detecting the onset of seizures can be implemented as a generic algorithm in a detection or monitoring system, which only uses a single EMG measuring channel to detect seizures. This enables the generic algorithm to be implemented in a small detection or monitoring device without having to calibrate the parameters, i.e. the threshold values, for each individual user first. This reduces the complexity of the detection system and reduces the number of components needed to detect seizures.

The described detection system may comprise an adaptive update module (not shown) which updates the threshold values each time the system has detected a seizure. This enables the first and second threshold values for the number of counts and time windows to be adjusted so that the system is able to detect the seizures more accurately. This in turn will reduce the number of false positives and also reduce the latency for the system.

EXAMPLE

Electromyographic measurements were conducted on six different persons of different ages and genders. The persons all had at least one tonic-clonic seizure which was verified by other measurements, including video and EEG measurements.

The EMG sensors were placed on the left deltoid muscle with the active electrode on the center of the muscle and the reference electrode placed on the acromioclavicular joint. The EMG signal was sampled with a sampling rate of 1024Hz. The measured EMG signals were pre-processed with a high-pass Butterworth filter with an order of 20 and a cut-off frequency of 150Hz and analysed with time windows with a length of 1 sec. and an overlap of 75% and a hysteresis value of ±50μV.

The described detection system has a sensitivity of 100%, meaning that it detected all the seizures. The detection system has a false detection rate (FDR) between 0 and 0.1885 per hour and a latency between 7 sec. and 10.5 sec.

The invention claimed is:

1. A system for detecting the onset of seizures, such as epileptic seizures with a monitoring or detection device, comprising:
   the monitoring or detection device,
   a measuring unit in the monitoring or detection device having at least one sensor having a configuration for detecting an electromyographic signal generated by a muscle on a body of a user; and
   a data processing unit in the monitoring or detection device connected to the measuring unit and configured to process and analyse the detected signal, wherein the data processing unit comprises:
      a pre-processing module having a high-pass filter configured to filter out signals having a frequency below a predetermined cut-off frequency,
      a feature extraction module connected to the pre-processing module and having a threshold detector, wherein the feature extraction module is configured to apply a first number of predetermined time windows to the filtered signal, and
      a classification module connected to the feature extraction module and configured to generate an output signal,
   wherein
      the feature extraction module is configured to count a number of crossings between the filtered signal and a predetermined hysteresis value defining a positive and a negative threshold value within each of the predetermined time windows and to count a number of zero-crossings of the filtered signal within each time window, and
      the classification module is configured to compare the count with a first threshold value, to compare the number of time windows having a count above the first threshold value, with a second threshold value and to generate the output signal if the number of time windows having a count above the first threshold value is above the second threshold value.

2. System according to claim 1, wherein the cut-off frequency is above 100Hz.

3. System according to claim 1, wherein the hysteresis value is between ±0µV and ±500µV.

4. System according to claim 1, wherein the predetermined time windows are configured as overlapping time windows having a predetermined overlap and length.

5. System according to claim 1, wherein the predetermined time windows have a length between 0.25 sec. and 2 sec.

6. System according to claim 4, wherein the predetermined time windows have the predetermined overlap between 0% and 95%.

7. System according to claim 1, wherein the system comprises at least a second measuring unit which is configured to detect the muscle activities of one or more muscles on the body of the user or another signal characteristic of a seizure, and at least a second data processing unit which is connected to the second measuring unit and configured to process and analyse the detected signal of the second measuring unit and further configured to generate an output signal indicating whether the detected signal is above a third threshold value or not.

8. System according to claim 7, wherein the classification modules in the data processing unit is further connected to an evaluation module which is configured to generate the event signal if two or more of the output signals of the classification modules have a higher output value than a predetermined hysteresis value or if a weighted sum of the output signals is above a fourth threshold value.

9. System according to claim 1, wherein the system further comprises an alarm unit connected to the data processing unit, wherein the alarm unit is configured to generate an alarm or an alarm message based on the event signal.

10. System according to claim 1, wherein the system is configured to detect seizures having tonic activity or tonic-clonic seizures.

11. System according to claim 2, wherein the cut-off frequency is between 100Hz and 200Hz.

12. System according to claim 3, wherein the hysteresis value is between ±20µV and ±250µV.

13. System according to claim 6, wherein the predetermined time windows have the predetermined overlap between 50% and 75%.

14. System according to claim 1, wherein the first threshold is between 240 and 300 crossing counts.

15. System according to claim 1, wherein the second threshold is between 1 and 40 crossing counts.

16. System according to claim 15, wherein the second threshold is between 10 and 25 crossing counts.

17. System according to claim 1, wherein the first threshold is between 100 and 400 crossing counts.

18. A method for indicating the onset of seizures, such as epileptic seizures with a monitoring or detection device, comprising the steps of:
providing the monitoring or detection device,
providing a measuring unit in the monitoring or detection device and a data processing unit connected to the measuring unit in the monitoring or detection device,
detecting one or more electromyographic signals generated by at least one muscle on the body of a user by means of the measuring unit and transmitting to the data processing unit,
processing and analysing the detected signal by means of the data processing unit in which the detected signal is filtered by means of a high-pass filter and a first number of predetermined time windows is applied to the filtered signal, and
generating an output signal by means of the data processing unit and triggering an event based on the output signal, further comprising:
counting a number of crossings between the filtered signal and a predetermined hysteresis value,
providing a feature extraction module in the data processing unit,
defining a positive and a negative threshold value within each of the first number of predetermined time windows by means of the feature extraction module,
counting a number of zero-crossings of the filtered signal within each time window,
generating a second number of time windows having a count above a first threshold value,
providing a classification module in the data processing unit and comparing the count with a first threshold value,
further comparing the second number of time windows to a second threshold value by means of the classification module, and
generating the event signal if the second number of time windows is above the second threshold value.

19. Method according to claim 18, wherein overlapping time windows of a predetermined length are applied to the filtered signal where the first number of time windows overlaps the second number of time windows with a predetermined overlap.

20. Method according to claim 18, wherein at least a second measuring unit detects the muscle activities of one or more muscles on the body of the user or another signal characteristic of a seizure, and at least a second data processing unit processes and analyses the detected signal of the second measuring unit and generates an output signal indicating whether the detected signal is above a third threshold value or not.

21. Method according to claim 20, wherein the output signals of the classification modules in the data processing unit are transmitted to an evaluation module which generates the event signal if two or more of the output signals have a higher output value than a predetermined hysteresis value or if a weighted sum of the output signals is above a fourth threshold value.

22. Method according to claim 18, wherein the event signal is transmitted to an alarm unit which generates an alarm or an alarm message based on the event signal.

23. Method according to claim 18, wherein the measuring unit and data processing unit detect seizures having tonic activity or tonic-clonic seizures.

24. Method according to claim 18, wherein the first threshold is between 100 and 400 crossing counts.

* * * * *